US012222269B2

(12) United States Patent
Plasenzotti et al.

(10) Patent No.: US 12,222,269 B2
(45) Date of Patent: Feb. 11, 2025

(54) BLOOD COLLECTION TUBE FOR MEASURING BLOOD VISCOSITY, BLOOD VISCOSITY MEASUREMENT DEVICE, AND SEALED PACK OF BLOOD COLLECTION TUBE FOR MEASURING BLOOD VISCOSITY

(71) Applicants: MEDICAL UNIVERSITY OF VIENNA, Vienna (AT); KANSAI UNIVERSITY, Osaka (JP); TAISEI KAKO CO., LTD., Osaka (JP); ASAHI GROUP HOLDINGS, LTD., Tokyo (JP)

(72) Inventors: Roberto Plasenzotti, Himberg (AT); Bruno Karl Podesser, Vienna (AT); Hideki Yamamoto, Osaka (JP); Yusuke Negi, Osaka (JP); Takafumi Yabuta, Osaka (JP); Hidenari Nishikura, Osaka (JP); Eiji Tamura, Hyogo (JP); Kimito Kawamura, Ibaraki (JP)

(73) Assignees: MEDICAL UNIVERISITY OF VIENNA, Vienna (AT); KANSAI UNIVERSITY, Osaka (JP); TAISEI KAKO CO., LTD., Osaka (JP); ASAHI GROUP HOLDINGS, LTD., Tokyo (JP)

( * ) Notice: Subject to any disclaimer, the term of this patent is extended or adjusted under 35 U.S.C. 154(b) by 262 days.

(21) Appl. No.: 17/789,078

(22) PCT Filed: Dec. 27, 2019

(86) PCT No.: PCT/JP2019/051533
§ 371 (c)(1),
(2) Date: Jun. 24, 2022

(87) PCT Pub. No.: WO2021/131045
PCT Pub. Date: Jul. 1, 2021

(65) Prior Publication Data
US 2023/0042810 A1  Feb. 9, 2023

(51) Int. Cl.
*G01N 11/12* (2006.01)
*G01N 33/49* (2006.01)

(52) U.S. Cl.
CPC ............. *G01N 11/12* (2013.01); *G01N 33/49* (2013.01)

(58) Field of Classification Search
CPC .. G01N 11/12; G01N 33/49; A61B 5/150389; A61B 5/150473;
(Continued)

(56) References Cited

U.S. PATENT DOCUMENTS 3,055,367 A * 9/1962 Thorstad ............... A61J 1/2089
222/490
4,388,823 A 6/1983 Garnaud
(Continued)

FOREIGN PATENT DOCUMENTS

CA   611575 A   12/1960
JP   3000726 U   8/1994
(Continued)

OTHER PUBLICATIONS

Search report in corresponding EP 19957871.7 dated Jul. 10, 2023 (pp. 1-12).
(Continued)

*Primary Examiner* — Robert R Raevis
(74) *Attorney, Agent, or Firm* — Millen, White, Zelano & Branigan; William F. Nixon

(57) ABSTRACT

A blood-viscosity measurement blood collection tube includes a bottomed tube provided with an opening at one end in a length direction and a bottom at the other in the length direction, and a sealing plug. The sealing plug
(Continued)

includes a sealing part fitted in the opening of the bottomed tube in a hermetically sealed state, a cap part, and a thin connecting part. The sealing part includes a vertically penetrated insertion hole. The sealing part of the sealing plug is fitted in the opening of the bottomed tube, and an inner space of the bottomed tube is in a negative pressure state. The cap part is configured to be removed from the sealing plug by breaking the connecting part with an external force applied to the cap part, and the insertion hole is exposed at an upper surface of the sealing part when the cap part has been removed.

5 Claims, 9 Drawing Sheets

(58) Field of Classification Search
CPC ............... A61B 5/15003; A61B 5/157; A61B 5/150351; B01L 2300/041; B01L 2300/046; B01L 3/50825
USPC ........... 73/54.01, 54.13, 54.15, 54.19, 54.21, 73/64.56, 864, 864.52, 864.74; 141/66, 141/94
See application file for complete search history.

(56) References Cited

U.S. PATENT DOCUMENTS

| | | |
|---|---|---|
| 4,517,830 A | 5/1985 | Gunn |
| 5,203,203 A | 4/1993 | Bryan et al. |
| 5,634,474 A | 6/1997 | Grippi |
| 6,364,143 B1 | 7/2002 | Knierbein |
| 2005/0059163 A1 | 3/2005 | Dastane et al. |

FOREIGN PATENT DOCUMENTS

| | | | |
|---|---|---|---|
| JP | H08219973 A | | 8/1996 |
| JP | H09243542 A | | 9/1997 |
| JP | 2001527438 A | * | 12/2001 |
| JP | 2002520093 A | | 7/2002 |
| JP | 2006208260 A | | 8/2006 |
| JP | 2007127468 A | | 5/2007 |
| JP | 2007127469 A | | 5/2007 |
| JP | 2007127470 A | | 5/2007 |
| JP | 2007127471 A | | 5/2007 |
| JP | 2008278830 A | | 11/2008 |

OTHER PUBLICATIONS

English Translation of International Search Report for PCT/JP2019/051533 dated Feb. 18, 2020.

English Abstract of JP2007127468, Publication Date: May 24, 2007.

English Abstract for JP2008278830, Publication Date: Nov. 20, 2008.

English Abstract of JP2006208260, Publication Date: Aug. 10, 2006.

English Abstract for JPH08219973, Publication Date: Aug. 30, 1996.

* cited by examiner

BLOOD COLLECTION TUBE FOR MEASURING BLOOD VISCOSITY, BLOOD VISCOSITY MEASUREMENT DEVICE, AND SEALED PACK OF BLOOD COLLECTION TUBE FOR MEASURING BLOOD VISCOSITY

TECHNICAL FIELD

The present invention relates to a blood collection tube in which a blood collection tube that has collected blood can be used as a blood-viscosity measurement container as it is and can initiate blood-viscosity measurement within a very short time after collecting the blood, and also relates to a blood-viscosity measurement device.

In this specification and claims, the term "negative pressure" means that the absolute pressure is 50 kPa or less. Further, in this specification and claims, the term "rubber" is used in a sense including a thermoplastic elastomer.

BACKGROUND OF THE INVENTION

In recent years, the interest in the viscosity of human blood has been increased. It is said that if such blood viscous properties can be grasped, it becomes possible to predict blood diseases and detect diseases at an early stage.

Conventionally, a falling ball type blood-viscosity measurement device is known (see Patent Document 1). In the falling ball type blood-viscosity measurement device, blood is collected with a syringe in which a steel ball is disposed to measure the blood viscosity, and the steel ball is raised to an upper position in the syringe using a magnetic force. Thereafter, the steel ball is dropped, and the fall terminal velocity of the falling steel ball is measured to determine the blood viscosity.

Further, as a device for measuring fluid viscosity, a falling body type viscosity measurement device is known in which fluid viscosity is determined by measuring the fall terminal velocity of a cylindrical falling body that falls in a cylindrical measurement container filled with a fluid (see Patent Document 2).

PRIOR ART DOCUMENT

Patent Document

Patent Document 1: U.S. Pat. No. 4,388,823
Patent Document 2: Japanese Unexamined Patent Application Publication No. H08-219973

SUMMARY OF THE INVENTION

Problems to be Solved by the Invention

In the blood-viscosity measurement device described in the above-described Patent Document 1, the steel ball in the syringe is raised to an upper position in the syringe by a magnetic force from the outside. In this case, it is required to move the steel ball in a viscous blood fluid from a remote location, which requires a very strong magnetic force. Further, when the steel ball drops, the steel ball often comes into contact with the inner wall of the syringe, which prevents highly accurate viscosity measurement.

Further, blood gradually coagulates by the coagulation action when exposed to air, and therefore, an anticoagulant is added to the sampled blood in a normal blood test. Adding this anticoagulant does not significantly impact ingredient analyses, but it significantly impacts viscosity measurement to assess the blood status. Therefore, in order to measure the viscosity of blood, it is desirable to complete the viscosity measurement within three minutes after the blood collection without adding an anticoagulant so that the blood solidification does not start.

However, according to the viscosity measurement device of Patent Document 2 described above, there are the following problems. That is, in measuring the blood viscosity, it requires an operation of transferring the blood collected in the blood collection tube to the measurement container of the viscosity measurement device. This took time, although not exceeding three minutes, to initiate the viscosity measurement after collecting the blood. Further, when transferring the sampled blood to a measurement container, it is also concerned that the sampled blood will have more chance to come into contact with the atmosphere, promoting blood coagulation.

Under the circumstance, there has been a need to develop a means and a method capable of shortening the time from when the blood is collected until when the viscosity measurement is initiated, preventing the sampled blood from coming into contact with the air, and quickly initiating dropping of the falling body.

The present invention has been made in view of the above-described technical background. An object of the present invention is to provide a blood-viscosity measurement blood collection tube and a blood-viscosity measurement device in which a blood collection tube that has collected blood can be used as a blood-viscosity measurement container as it is, the blood-viscosity measurement can be quickly initiated without for the measurer coming into contact with the blood, and the blood-viscosity measurement can be performed in a substantially air non-contact manner.

Means for Solving the Problem

In order to achieve the above-described objective, the present invention provides the following measures.

[1] A blood-viscosity measurement blood collection tube, comprising:
  a bottomed tube provided with an opening at one end in a length direction and a bottom at the other end in the length direction; and
  a sealing plug,
  wherein the sealing plug is provided with a sealing part capable of being fitted in the opening of the bottomed tube in a hermetically sealed state, a cap part, and a thin connecting part connecting the cap part and the sealing part,
  wherein the sealing part is provided with a vertically penetrated insertion hole,
  wherein the sealing part of the sealing plug is fitted in the opening of the bottomed tube, and an inner space of the bottomed tube is in a negative pressure state, and
  wherein the cap part is configured to be removed from the sealing plug by breaking the connecting part with an external force applied to the cap part, and the insertion hole is exposed at an upper surface of the sealing part when the cap part is removed.

[2] The blood-viscosity measurement blood collection tube as recited in the above-described Item [1], further comprising:
  a guide tube communicated with the insertion hole, the guide tube being secured to the sealing part in a downwardly extended manner.

[3] The blood-viscosity measurement blood collection tube as recited in the above-described Item [1] or [2], wherein the guide tube is provided with one or a plurality of apertures or slits formed on a side surface of the guide tube.

[4] A blood-viscosity measurement device comprising:
a viscosity measurement falling body;
the blood-viscosity measurement blood collection tube as recited in any one of the above-described Items [1] to [3]; and
a detector configured to detect a fall terminal velocity or fall acceleration of a viscosity measurement falling body which is falling in the blood collection tube.

[5] A blood-viscosity measurement blood collection tube sealed pack, comprising:
the blood-viscosity measurement blood collection tube as recited in any one of claims 1 to 4; and
a vacuum pack in which the blood-viscosity measurement blood collection tube is hermetically sealed in a vacuumed state.

Effects of the Invention

In the invention as recited in the above-described Item [1], it is possible to use the blood collection tube that has collected blood as a measurement container as it is. Further, the measurer can quickly initiate the blood-viscosity measurement without coming into contact with the blood. It is also capable of measuring the blood viscosity substantially in an air non-contact manner. The inside of the blood collection tube is in a negative pressure state, and therefore, it is possible to collect the quantity of blood required for the blood-viscosity measurement at the time of the blood collection. Further, by defining (controlling) the internal pressure of the blood collection tube with high accuracy, the quantity of blood to be collected can be kept constant at all times.

In the invention as recited in the above-described Item [2], since the guide tube extended downward is secured, it is possible to assuredly guide the viscosity measurement falling body to the measurement position of the bottomed tube by the guide tube to measure the blood viscosity more accurately.

In the invention as recited in the above-described Item [3], since one or a plurality of apertures or slits are formed on the side surface of the guide tube, the viscosity measurement falling body can smoothly drop the inside of the guide tube while discharging the air in the guide tube, which enables further accurate blood-viscosity measurement.

In the invention as recited in the above-described Item [4], it is possible to use the blood collection tube that has collected blood as a blood-viscosity measurement container as it is, thereby enabling the measurer to quickly initiate the blood-viscosity measurement without touching the blood. It is also possible to provide a blood-viscosity measurement device capable of measuring the blood-viscosity in a substantial air non-contact manner.

In the invention as recited in the above-described Item [5], since the blood collection tube is sealed in the vacuum pack, the negative pressure state in the blood collection tube can be maintained for a long period of time. Thus, by opening the vacuum pack at the time of use, it is possible to provide a blood collection tube in which the inside is in a sufficiently negative pressure.

EMBODIMENTS FOR CARRYING OUT THE INVENTION

Figure 1:
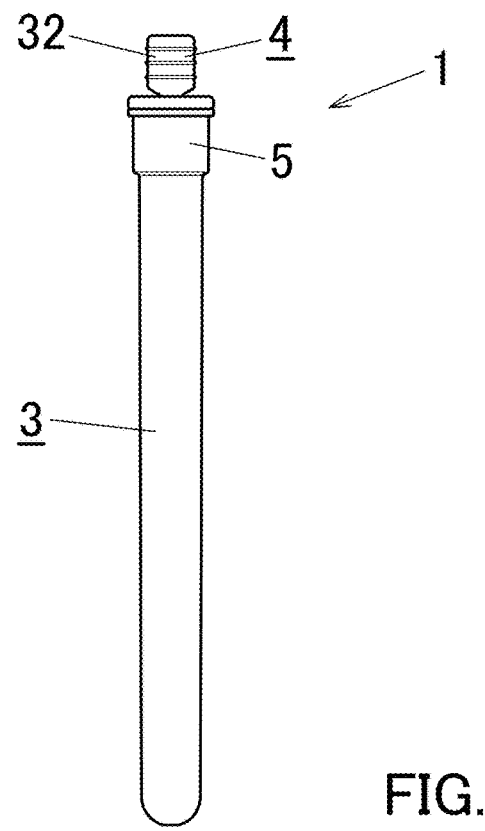
FIG. 1 is a front view showing one embodiment of a blood-viscosity measurement blood collection tube according to the present invention.
Figure 2:
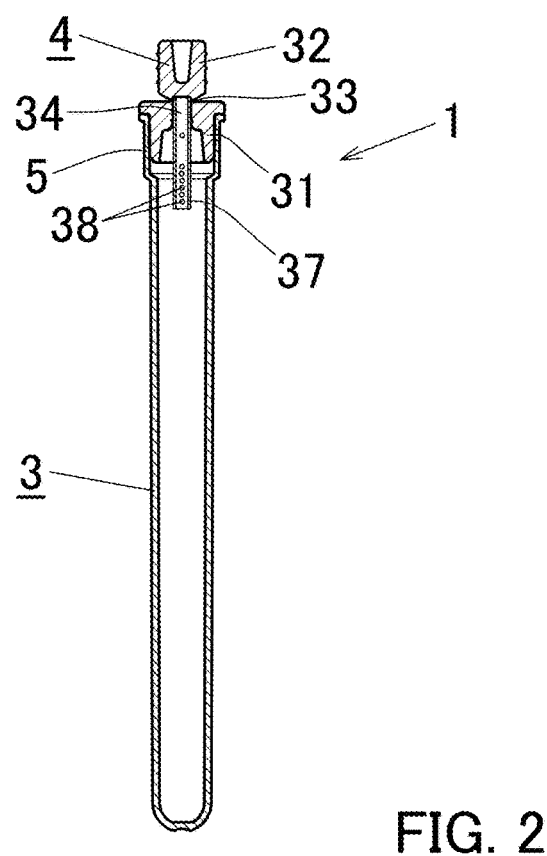
FIG. 2 is a vertical cross-sectional view of the blood-viscosity measurement blood collection tube of FIG. 1.

A blood-viscosity measurement blood collection tube 1 according to the present invention is provided with a bottomed tube 3 and a sealing plug 4 (see FIGS. 1 and 2).

Figure 3:
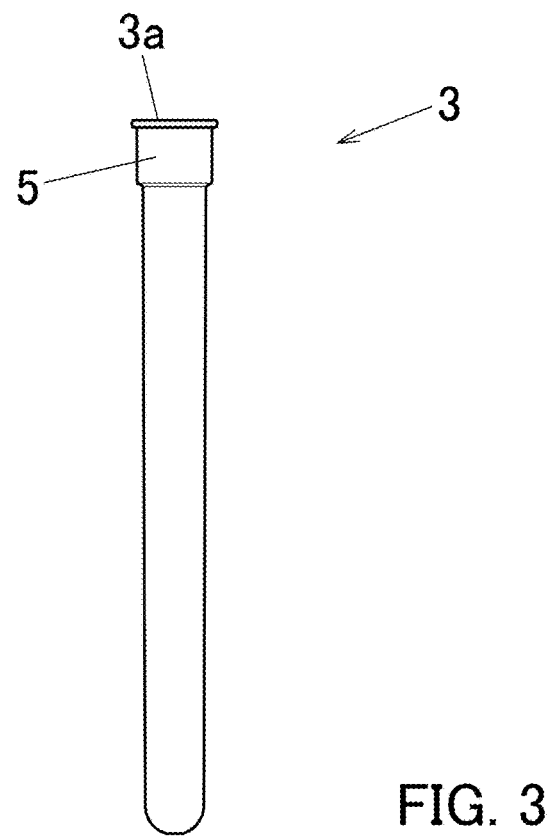
FIG. 3 is a front view of a bottomed tube.
Figure 4:
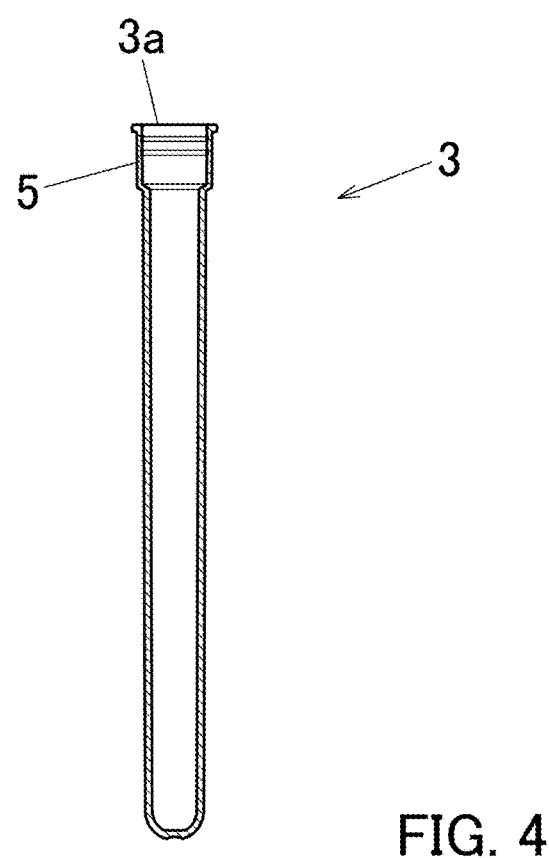
FIG. 4 is a vertical cross-sectional view of the bottomed tube of FIG. 3.

The bottomed tube 3 is a tube body, as shown in FIGS. 3 and 4, provided with an opening 3a at one end side (upper side in the drawing) in the length direction and a bottom wall at the other end side (lower side in the drawing) in the length direction. The bottomed tube 3 is a cylindrical bottomed tube having a constant diameter over substantially the entire length. The bottomed tube 3 has a structure provided at the end side of the opening 3a with an enlarged diameter portion 5 enlarged in diameter. It is desirable that the bottomed tube 3 be transparent.

The material of the bottomed tube 3 is not particularly limited but may be made of, for example, polyester resin (PET, PEN, PBT), polyolefin resin (PP, PE) or cyclic olefin resin (COP, COC), or the like. Among these, it is preferably made of polyester resin, and particularly preferably made of polyethylene terephthalate (PET). By being made of polyethylene terephthalate (PET), it is possible to sufficiently suppress solidifying adhesion of the blood to the inner surface of the bottomed tube 3, which enables more accurate blood-viscosity measurement.

Figure 5:
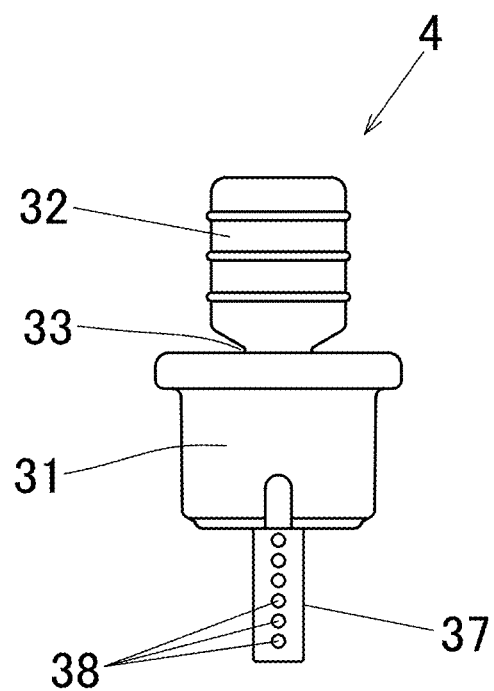
FIG. 5 is a front view of a sealing plug with a guide tube.
Figure 6:
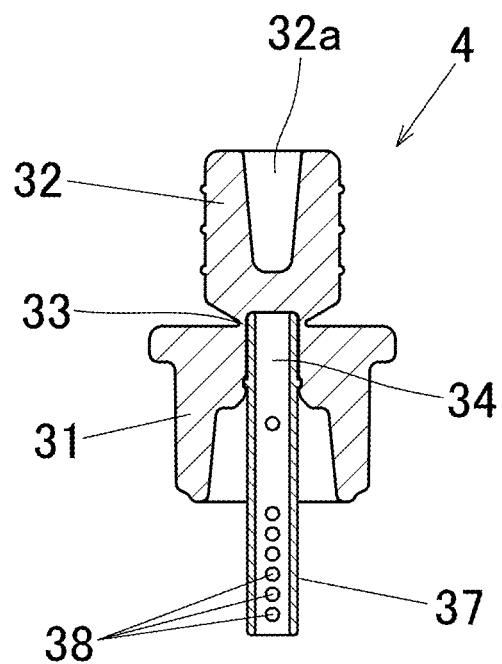
FIG. 6 is a vertical cross-sectional view of the sealing plug with the guide tube of FIG. 5.

As shown in FIGS. 5 and 6, the sealing plug 4 is provided with a sealing part 31 capable of being fitted into the opening 3a of the bottomed tube in a hermetically sealed state, a cap part 32 capable of being pinched by fingers, and a connecting part 33 connecting the cap part 32 and the sealing part 31. The connecting part 33 is a connecting part made of an annular member with a thin thickness (thickness in the horizontal direction). The cap part 32 has an outer diameter shape formed in a substantially cylindrical shape. At the upper surface of the cap part 32, a needle insertion hole 32a is provided (see FIG. 6).

The material of the sealing plug 4 is not particularly limited. It may be made of various rubber materials, such as, e.g., natural rubber, butyl rubber, isoprene rubber, butadiene rubber, styrene-butadiene rubber, and silicone rubber, and various thermoplastic elastomers, such as, e.g., polyurethane-based thermoplastic elastomer, polyester-based thermoplastic elastomer, polyamide-based thermoplastic elastomer, olefin-based thermoplastic elastomer, and styrene-based thermoplastic elastomer. Of these, it is particularly preferred to be made of butyl rubber. In a case where it is made of butyl rubber, the degree of the hermetical sealing by the sealing plug is high, which enables maintaining the inside of the blood collection tube in a higher negative pressure condition. Therefore, it is possible to collect a sufficient quantity of blood in the blood collection tube when collecting blood, which enables more accurate blood-viscosity measurement.

Figure 7:
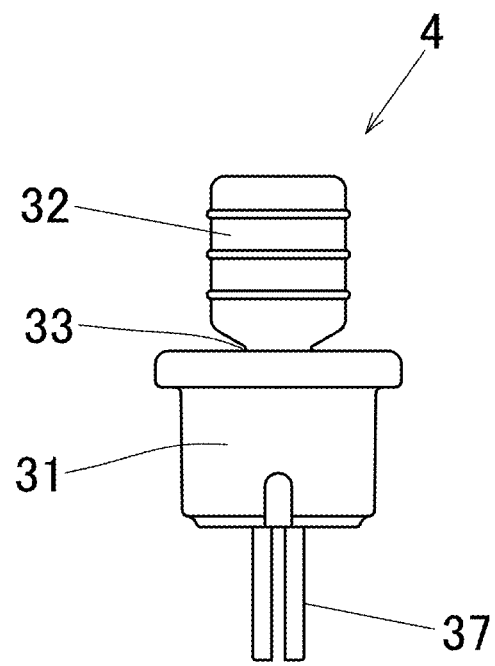
FIG. 7 is a front view showing another example of a sealing plug with a guide tube.
Figure 8:
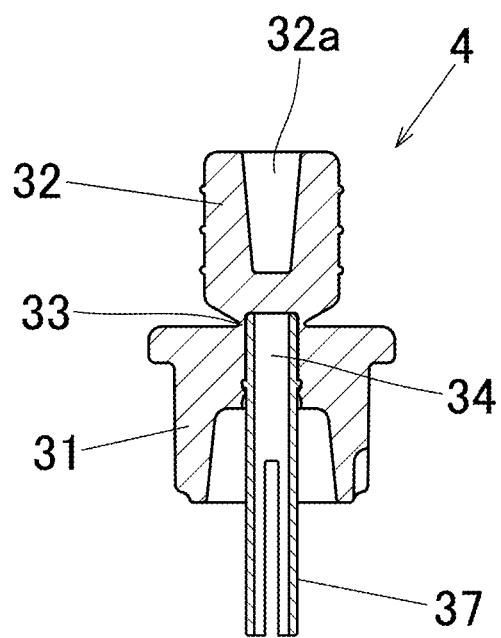
FIG. 8 is a vertical cross-sectional view of the sealing plug with the guide tube of FIG. 7.

The sealing part 31 is provided with a vertically penetrated insertion hole 34. A guide tube 37 communicating with the insertion hole 34 is fitted in the insertion hole 34 such that the guide tube 37 extends downward (see FIG. 6). The planar shape of the insertion hole 34 is circular. The guide tube 37 is a cylindrical tube. A plurality of apertures (through-holes) 38 is formed in the side surface of the guide tube 37. In this embodiment, a circular aperture 38 is formed, but the present invention is not particularly limited to such a shape. For example, as shown in FIGS. 7 and 8, a slit 39 may be formed.

The material of the guide tube 37 is not particularly limited and may be made of various rubber materials, such as, e.g., polyester resin (PET, PEN, PBT), polyolefin resin (PP, PE), cyclic olefin resins (COP, COC), natural rubber, butyl rubber, isoprene rubber, butadiene rubber, styrene-butadiene rubber, and silicone rubber, and various thermoplastic elastomers, such as, e.g., polyurethane-based thermoplastic elastomer, polyester-based thermoplastic elastomer, polyamide-based thermoplastic elastomer, olefin-based thermoplastic elastomer, and styrene-based thermoplastic elastomer. Among these, it is preferably made of polyester resin, particularly preferably made of polyethylene terephthalate (PET).

The upper end of the insertion hole 34 communicates with the inner space of the annular member constituting the connecting part 33 (see FIG. 6). The upper side of the insertion hole 34 is closed by the cap part 32 (see FIG. 6). The outer diameter of the annular member constituting the connecting part 33 is smaller than the outer diameter of the cap part 32 and smaller than the outer diameter of the sealing part 31 (see FIG. 6).

The blood-viscosity measurement blood collection tube 1 is a tube in which the sealing part 31 of the sealing plug 4 is fitted in the opening 3a of the bottomed tube 3 in a hermetically sealed state (see FIGS. 1 and 2). The sealing plug 4 is fitted in the opening of the bottomed tube 3 such that the notched part formed in the sealing part 31 of the sealing plug 4 extends beyond the opening of the bottomed tube 3 (in a half-sealed state). And the blood collection tube is brought into a vacuum chamber. Thereafter, the inside of the vacuum chamber is made in a negative pressure state to a specified value, and then the sealing part 31 of the sealing plug 4 is completely fitted to the bottomed tube 3 in the vacuum chamber (in a hermetically sealed state). Then, the collection tube is took out of the vacuum chamber. Since the sealing part 31 of the sealing plug 4 is tightly fitted in the opening 3a of the bottomed tube 3 in a hermetically sealed state, the inner space of the bottomed tube 3 can be maintained in the negative pressure state for a long period of time. At this time, the degree of vacuum (absolute pressure) in the blood collection tube 1 is preferably set to 30 kPa or less, more preferably set to 20 kPa or less. The cap part 32 can be removed by applying an external force (a tensile force, a shearing force, a torsional force, etc.) to the cap part 32 to break the connecting part 33. By removing the cap part 32, the insertion hole 34 for inserting a falling body appears (opens) at the upper surface of the sealing part 31. The connecting part 33 is formed of an annular member which is thin in thickness (the thickness in the horizontal, i.e., the thickness in the radial direction of the annular member), and therefore, the connecting part 33 can be easily broken by pulling the cap part 32 with the bottomed tube 3 held by a hand.

Next, an example of a blood-viscosity measurement method using the blood-viscosity measurement device 70 configured using the above-described blood collection tube 1 will be described.

Figure 9:
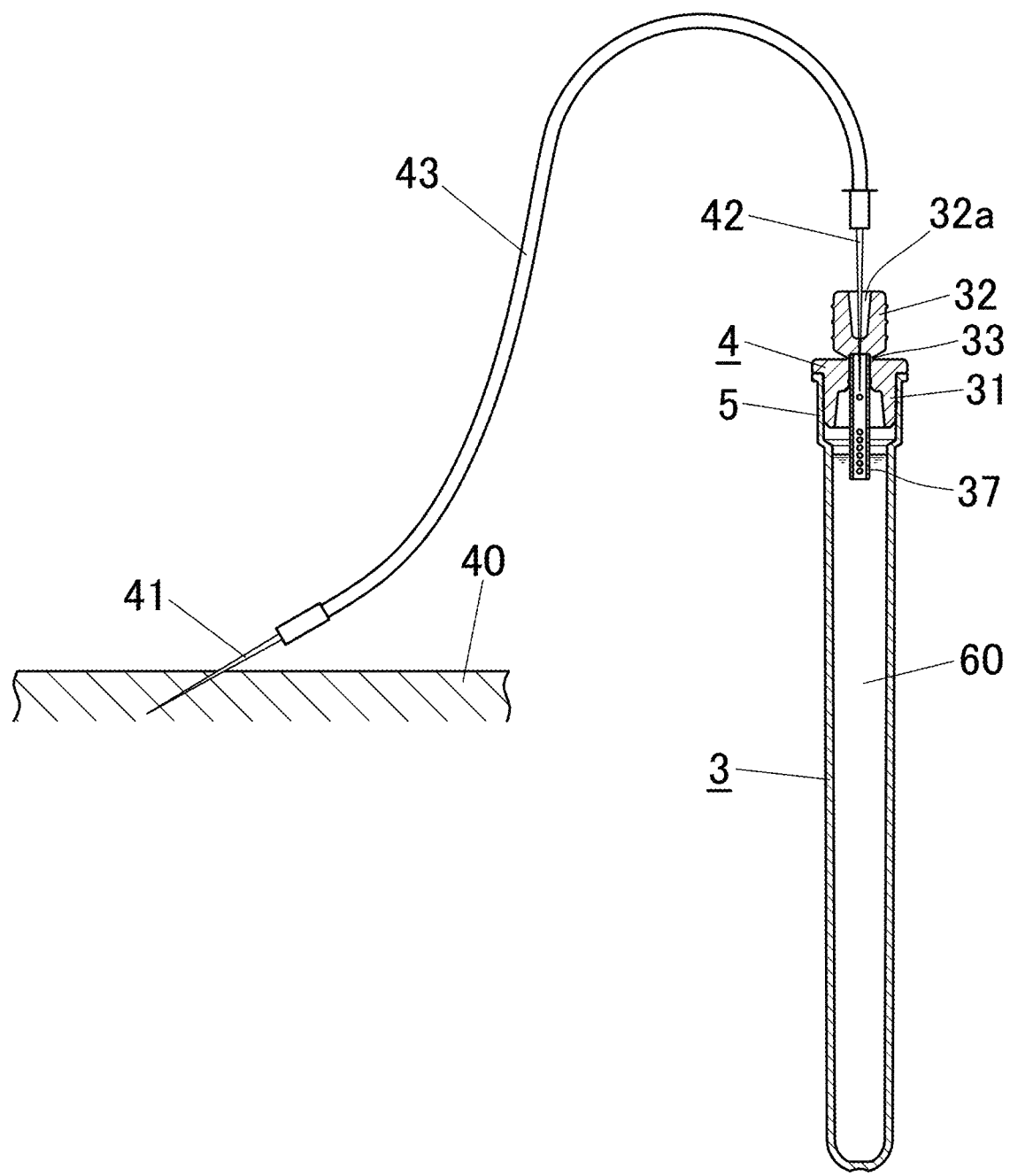
FIG. 9 is a diagram illustrating an example of a state when collecting blood.

As shown in FIG. 9, using a blood collection device provided with a tube 43 and needles 41 and 42 attached to both ends of the tube, one needle 41 is pierced into the skin 40 of a human body. Thereafter, the distal end of the other needle 42 is pierced through the cap part 32 by way of the needle insertion hole 32a of the cap part 32 of the blood-viscosity measurement blood collection tube 1 according to the present invention, and the distal end of the other needle 42 is placed in the insertion hole 34 (guide tube 37). As described above, the inside of the blood collection tube 1 (bottomed tube 3) has been set to be a negative pressure in advance. Accordingly, blood 60 is injected into the inside of the bottomed tube 3 via the one needle 41, the tube 43, and the other needle 42. Thus, the blood 60 is drawn into the bottomed tube 3 so that the lower end of the guide tube 37 is immersed in the blood 60 (see FIG. 9). As described above, it is preferable that the lower end portion of the guide tube 37 be immersed in the blood 60. In this case, it is possible to measure the blood-viscosity more precisely.

Figure 10:
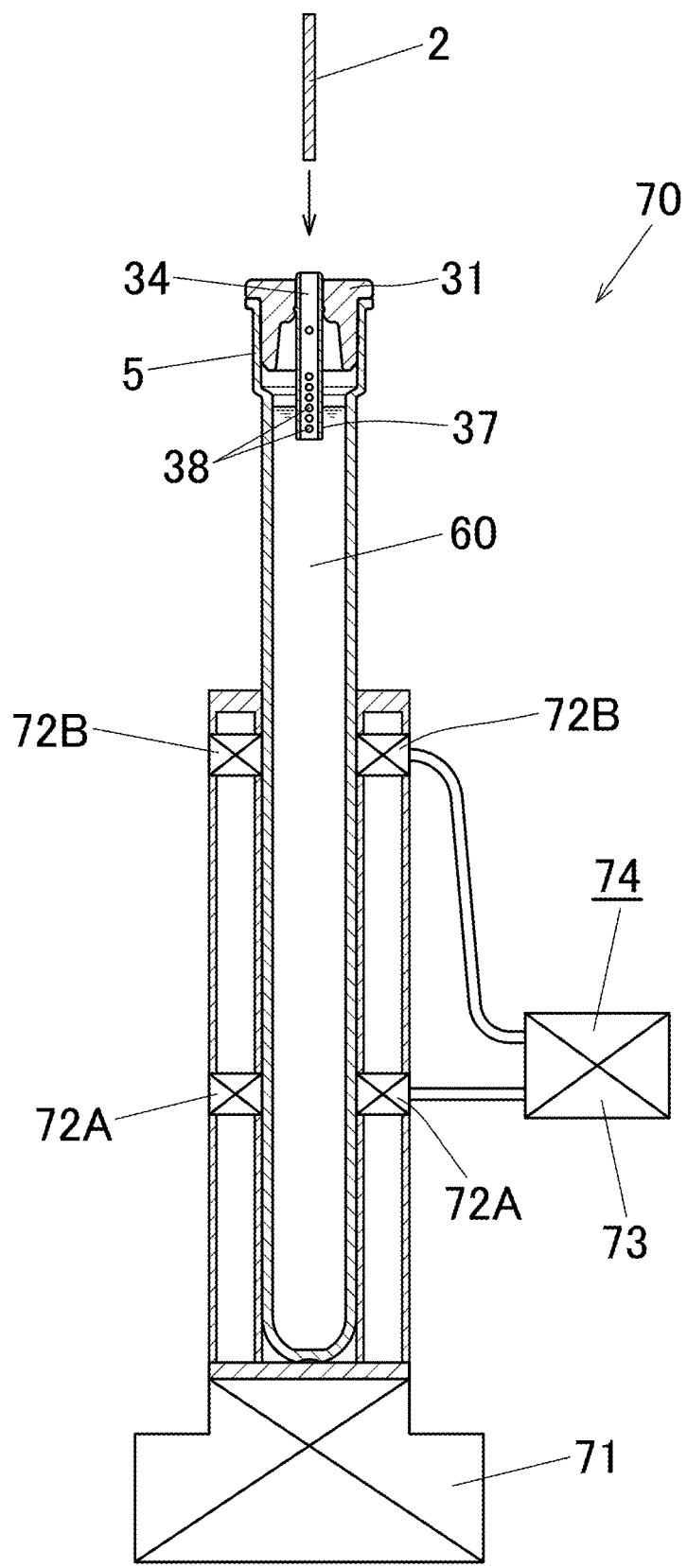
FIG. 10 is a partial cross-sectional view showing a state in which a blood-viscosity measurement blood collection tube (a cap part of a sealing plug has been removed) in which blood has been collected is set to a blood-viscosity measurement device.

Next, the connecting part 33 is broken (torn) to remove the cap part 32 by pulling the cap part 32 with fingers. As a result, the insertion hole 34 is exposed at the upper surface of the sealing part 31 as shown in FIG. 10. In this insertion hole 34, the upper end portion of the guide tube 37 has been inserted and fitted. This guide tube 37 is extending downward. Accordingly, as will be described in detail, the needle-like falling body 2 is assuredly guided by the guide tube 37 to the measuring position of the blood collection tube 1, which can realize the dropping of the substantially needle-like falling body 2 in the vertically downward direction (straight vertical falling to the bottom wall of the blood collection tube 1). Further, since a plurality of apertures 38 is formed in the side surface of the guide tube 37, the substantially needle-like falling body 2 can smoothly fall in the guide tube 37 while discharging the air in the guide tube 37.

Then, the blood collection tube 1 from which the cap part 32 has been removed is inserted into the vertically extended insertion hole provided in the measuring device main body 71 from above. That is, the blood collection tube 1 is set to the measuring device main body 71 to constitute a blood-viscosity measurement device 70 (see FIG. 10). A detection means 74 for detecting a fall terminal velocity of the substantially needle-like falling body 2 falling in the blood-viscosity measurement blood collection tube 1 is attached to the measuring device main body 71. In this embodiment, as the detection means 74, a pair of first magnetic sensors 72A and 72A arranged apart from each other in the horizontal direction, a pair of second magnetic sensors 72B and 72B arranged apart from each other in the horizontal direction, and a measurement device 73 are used (see FIG. 10). The lower first magnetic sensor 72A are spaced apart from the upper second magnetic sensor 72B. The measurement device 73 measures the time from when a detection signal was received from the upper second magnetic sensor 72B to when a detection signal was received from the lower first magnetic sensor 72A. With this measurement device 73, it is possible to measure the time required for the falling body 2 to fall from the position of the upper second magnetic sensor 72B to the position of the lower first magnetic sensor 72A. It should be noted that the "fall terminal velocity" denotes the velocity when a constant falling motion is being performed in the fluid.

Then, the substantially needle-like falling body 2 is released into the insertion hole 34 formed in the upper surface of the sealing part 31 (see FIG. 10) to drop the falling body in the vertically downward direction through the guide tube 37. At this time, the substantially needle-like falling body 2 falls in a stabilized state in the vertically downward direction in the blood 60 in the blood collection tube 1 and reaches the bottom surface of the blood collection tube 1. At this time, the fall terminal velocity Ut of the falling body 2 is calculated from the drop time of the falling body 2 determined by the magnetic sensors 72A and 72B and the measurement device 73 and the distance between the upper magnetic sensor 72B and the lower magnetic sensor 72A.

Figure 11:
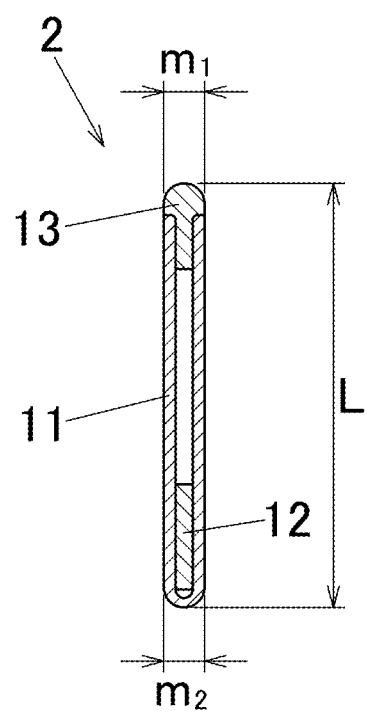
FIG. 11 is a cross-sectional view showing one example of a substantially needle-like falling body.

Note that in this embodiment, the substantially needle-like falling body 2 is a substantially needle-like body 11 made of synthetic resin in which a metal weight 12 is sealed therein. That is, in this embodiment, as shown in FIG. 11, a substantially needle-like falling body 2 is used in which a metal weight 12 is disposed inside a bottomed cylindrical substantially needle-like body 11 made of synthetic resin, and a lid 13 is fitted to the upper opening end of the substantially needle-like body 11. In this embodiment, the outer shape of the substantially needle-like falling body 2 is an axially elongated cylindrical shape (see FIGS. 10 and 11).

Next, a method of determining blood-viscosity using the obtained fall terminal velocity Ut of the falling body 2 will be described.

Figure 12:
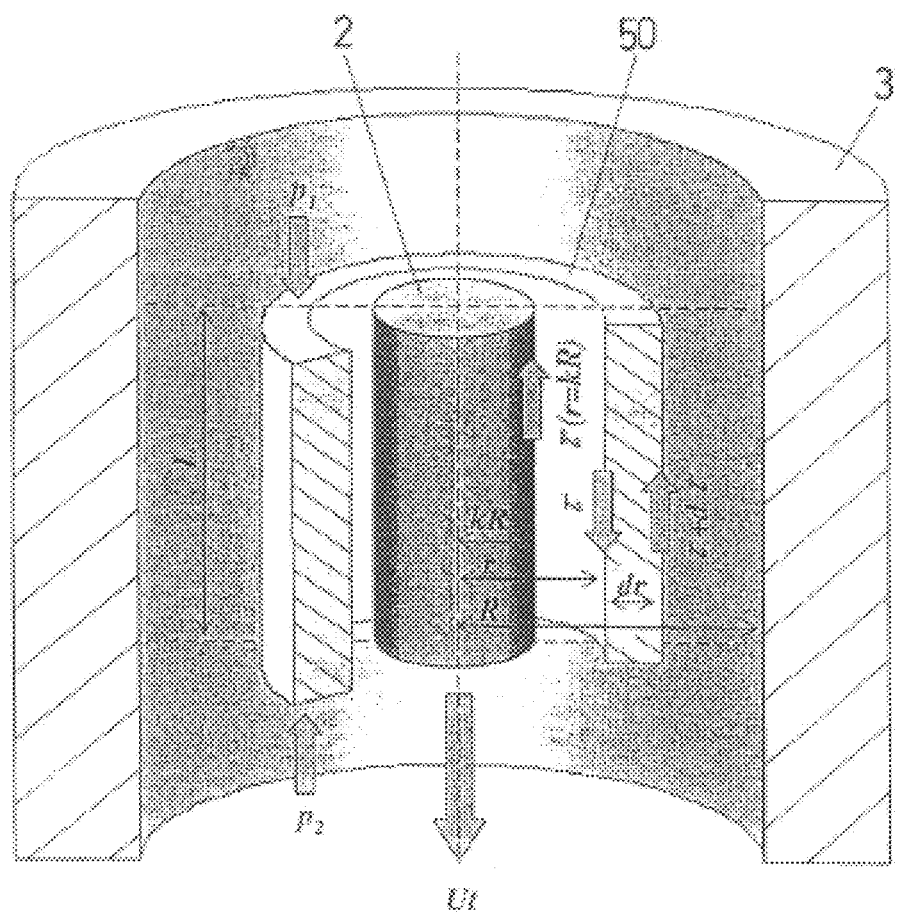
FIG. 12 is a conceptual diagram showing the state when the substantially needle-like falling body is falling.
Figure 13:
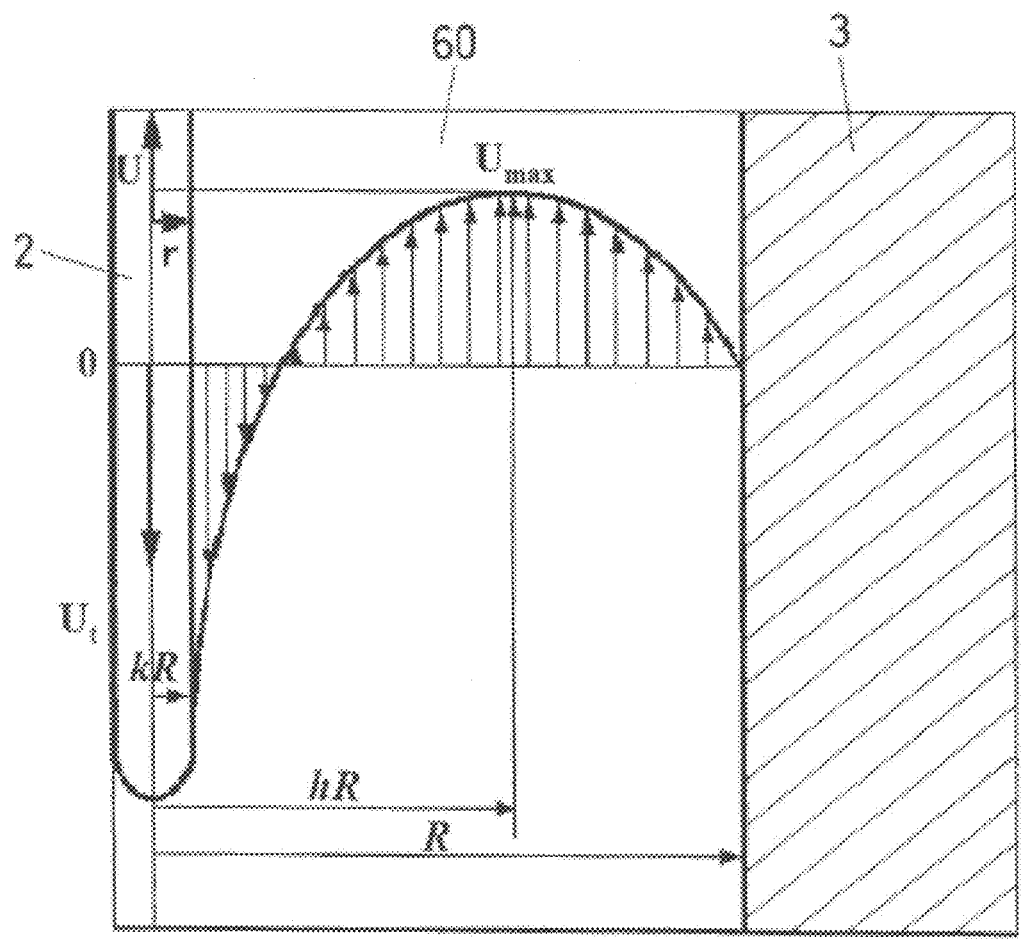
FIG. 13 is a velocity cross-sectional view showing moving directions of blood displaced by the dropping substantially needle-like falling body.

FIG. 12 is a conceptual diagram showing a state when the falling body 2 is dropping. FIG. 13 is a velocity cross-sectional view showing the moving directions of the blood 60 displaced by the dropping falling body 2. In these FIGS. 12 and 13, the reference symbol "L" denotes the length of the substantially needle-like falling body 2, The reference symbol "kR" denotes the radius of the substantially needle-like falling body 2, and the reference symbol "R" denotes the radius of the bottomed tube 3. Further, the reference numeral "50" denotes a minute cylindrical shell as a fluidic element around the falling body, the minute cylindrical shell being displaced by the dropping falling body. The reference symbol "r" denotes the inner radius of the minute cylindrical shell. The reference symbol "r+dr" denotes the outer radius of the minute cylindrical shell. The reference symbol "L" denotes the length of the minute cylindrical shell.

The fall velocity of the substantially needle-like falling body 2 is as very small as 0.1 mm/sec (0.1×10⁻³ m/sec) to 1.827 m/sec, and therefore no slippage occurs between the blood and the falling body and between the blood and the inner wall of the bottomed tube. Under the condition (assumption) that the blood is incompressible and that the in-tube flow is laminar, when the substantially needle-like falling body 2 falls at the fall terminal velocity Ut in the center of the blood 60 filled in the bottomed tube 3, the pressure p1 and the pressure p2 act on the upper surface and the lower surface of the minute cylindrical shell 50, respectively, and the shear stress τ and the shear stress τ+dτ act on the inner surface and the outer surface, respectively, as shown in FIG. 12. Since the blood is in a constant velocity dropping motion, the momentum acceleration is 0. Therefore, the following relational Equation <1> is established from the balance of the force acting on the minute cylindrical shell 50 at this time.

$$\frac{1}{r}\frac{d(r\tau)}{dr} = \frac{\Delta p}{L} \qquad <1>$$

where $\Delta p = p1-p2$ ($\Delta p<0$)

Further, at this time, since it is assumed that no slipping occurs between the wall surface of the falling body 2 and the inner wall surface of the bottomed tube 3, the following relational Equation <2> is established as a boundary condition relating to the speed.

$$u_{(r=kR)} = -U_\tau, u_{(r=R)} = 0 \qquad <2>$$

Further, since the quantity of the blood that passes through the annular flow path formed between the wall surface of the bottomed tube 3 and the inner wall surface of the bottomed tube 3 per unit time is equal to the quantity of the blood pushed aside by the falling body 2, the following Equation <3> is established.

$$Q=\int_{kR}^{R} 2\pi r u\, dr = \pi (kR)^2 U_\tau \qquad <3>$$

Further, on the wall surface of the falling body 2, the gravity, the buoyancy, the pressure, and the viscous forces are balanced, and therefore, the following Equation <4> is established. In Equation <4>, $\rho_s$ is the density of the falling body, and $\rho_f$ is the density of the blood.

$$(\rho_s - \rho_f)g + \frac{\Delta P}{L} = \frac{2\tau_{(r=kR)}}{kR} \qquad <4>$$

The viscosity of the blood can be analyzed by simultaneously combining the above-described Equation <5>, which is a constitutive Equation of the blood (a constitutive equation of Newton fluid), with the above-described Equations <1> to <4>. That is, since the blood is a Newton fluid in a state prior to solidification, the viscosity of the blood can be analyzed by simultaneously combining the Equation <5>, which is the constitutive Equations of Newton fluid, with the Equations <1> to <4>. For example, the blood-viscosity is obtained for each of a plurality of substantially needle-like falling bodies 2 having different densities, and these averages are adopted as a measured value of the blood-viscosity.

$$\tau = \mu \gamma \qquad <5>$$

In Equation <5>, "τ" is the shear stress, "γ" (gamma) is the shearing rate, and "μ" (mu) is the viscosity of the blood.

According to the blood-viscosity measurement device 70 having the above-described configuration, it is possible to use the blood collection tube 1 in which the blood has been collected as a measurement container as it is. The measurer can initiate the blood-viscosity measurement very quickly without coming into contact with the blood. Further, it is also possible to measure the blood-viscosity in a substantially non air-contact manner.

In the above-described embodiment, the detection means 74 is composed of the magnetic sensors 72A and 72B and the measurement device 73, but the present invention is not particularly limited to such a structure. The detection means 74 may be any means that can detect the fall terminal velocity of the dropping falling body 2.

Further, in the above-described embodiment, the viscosity of the blood is determined by measuring the fall terminal velocity of the falling body 2. But instead of this, the viscosity of the blood may be determined by measuring the fall acceleration of the falling body 2. As a detection means for measuring the fall acceleration of the falling body, a configuration composed of three or more magnetic sensors arranged apart from each other in the vertical direction (in the falling direction of the falling body) can be exemplified.

In the blood-viscosity measurement blood collection tube 1, it is preferable that an inner space of the bottomed tube 3 sealed with the sealing plug 4 be set in a negative pressure state and stored in a vacuum pack made of, for example, aluminum. It is preferable that the vacuum pack be opened to use the blood-viscosity measurement blood collection tube in the manner described above when it is used. In this manner, by encapsulating the blood collection tube in the vacuum pack, the negative pressure condition in the blood collection tube 1 can be maintained for a long period of time.

In the present invention, the synthetic resin (e.g., a synthetic resin constituting the substantially needle-like body 11) constituting the substantially needle-like falling body 2 is not particularly limited, but olefin resin, such as, e.g., polyethylene and polypropylene, is preferably used. In this case, it is possible to assuredly prevent blood from sticking to the surface of the falling body 2, which in turn enables viscosity measurement of blood with higher accuracy. The metal weight 12 may be in any form, such as, e.g., a mass, a granule, a powder, or the like.

Note that, in the above-described embodiment, as the falling body 2, a falling body made of a synthetic resin in which the metal weight 12 is encapsulated therein is used, but is not particularly limited to such a configuration.

Although there is no particular limitation on the size of the substantially needle-like falling body 2, from the viewpoint of enabling the viscosity measurement with a smaller quantity of blood and improving the accuracy of the viscosity measurement (see FIG. 11), it is preferable that the outer diameter ($m_1$, $m_2$) be set in the range of 0.5 mm 3 mm, and the length L be set in the range of 5 mm to 100 mm. In FIG. 9, it may be configured such that any of the relations $m_1=m_2$, $m_1>m_2$, $m_1<m_2$, is satisfied.

It should be noted that the density of the falling body 2 denotes the apparent density, which is a value obtained by dividing the mass of the falling body 2 by the volume (volume including voids) of the falling body 2.

EXAMPLES

Next, some specific examples of the present invention will be described, but it should be noted that the present invention is not particularly limited to those of the examples.

Example 1

As shown in FIG. 9, by collecting blood using a blood collection device (e.g., a needle), blood of a mammalian animal was collected into the inside of the blood-viscosity measurement blood collection tube shown in FIGS. 1 and 2 (in a high-internal negative pressure condition). Blood was collected into the bottomed tube 3 until the lower end of the guide tube 37 was submerged in the blood 60 (see FIG. 9). Then, the cap part of the sealing plug 4 was pinched with fingers and was torn to expose the insertion hole 34 penetrated vertically at the top surface of the sealing part. Thereafter, the blood collection tube was set to the blood-viscosity measurement device as shown in FIG. 10. Next, the viscosity measurement of the blood was performed according to the procedures described in the previous section using the blood-viscosity measurement device shown in FIG. 10. The inner diameter of the blood collection tube was about 10 mm, the length was about 140 mm, and the inner volume of the blood collection tube was about 11 mL. The length of the substantially needle-like falling body was 20 mm, and the outer diameter ($m_1$, $m_2$) was 2 mm. The apparent density of the substantially needle-like falling body was 1.486 g/cm$^3$. In addition, the density of the collected blood was 1.048 g/cm$^3$.

The time required for the substantially needle-like falling body 2 to fall from the position of the upper second magnetic sensor 72B to the position of the lower first magnetic sensor 72A was 0.04375 seconds, and the fall terminal velocity Ut of the falling body obtained from this was 33.1 cm/second.

The viscosities μ of the blood was calculated by simultaneously combining the four equations of Equations (1) to (4) and the constitutive Equation (5) of a Newton fluid. The viscosity μ of this blood was found to be 4.508 mPa sec.

INDUSTRIAL APPLICABILITY

The blood-viscosity measurement blood collection tube according to the present invention is used as a blood collection tube for collecting blood subject to viscosity measurement and is used as a measurement container (measuring cell) as it is in the case of blood-viscosity measurement. As described above, since it can be used as it is as a measurement container after the blood collection, the viscosity measurement of the blood can be initiated in a very short time after collecting the blood. Therefore, the blood viscosity measurement can be performed with high accuracy, and therefore, it can be useful for predicting blood diseases, early detection of diseases, and the like.

DESCRIPTION OF SYMBOLS

1: Blood-viscosity measurement blood collection tube
2: Falling body
3: Bottomed tube
3a: Opening
4: Sealing plug
31: Sealing part
32: Cap part
33: Connecting part
34: Insertion hole
37: Guide tube
38: Aperture
39: Slit
60: Blood
70: Blood-viscosity measurement device
74: Detector

The invention claimed is:

1. A blood-viscosity measurement blood collection tube, comprising:
  a bottomed tube provided with an opening at one end in a length direction and a bottom at the other end in the length direction; and
  a sealing plug,
  wherein the sealing plug is provided with a sealing part capable of being fitted in the opening of the bottomed tube in a hermetically sealed state, a cap part, and a thin connecting part connecting the cap part and the sealing part,
  wherein the sealing part is provided with a vertically penetrated insertion hole, wherein the sealing part of the sealing plug is fitted in the opening of the bottomed tube, and an inner space of the bottomed tube is in a negative pressure state, and wherein the cap part is configured to be removed from the sealing plug by breaking the connecting part with an external force applied to the cap part, and the insertion hole is exposed at an upper surface of the sealing part when the cap part is removed.

2. The blood-viscosity measurement blood collection tube as recited in claim 1, further comprising:

a guide tube communicated with the insertion hole, the guide tube being secured to the sealing part in a downwardly extended manner.

3. The blood-viscosity measurement blood collection tube as recited in claim 1, wherein the guide tube is provided with one or a plurality of apertures or slits formed on a side surface of the guide tube.

4. A blood-viscosity measurement device comprising:

a viscosity measurement falling body;

a blood-viscosity measurement blood collection tube as recited in claim 1; and a detector configured to detect a fall terminal velocity of a viscosity measurement falling body which is falling in the blood collection tube.

5. A blood-viscosity measurement blood collection tube sealed pack, comprising:

the blood-viscosity measurement blood collection tube as recited in claim 1; and a vacuum pack in which the blood-viscosity measurement blood collection tube is hermetically sealed in a vacuumed state.

* * * * *